United States Patent [19]

Ueno et al.

[11] Patent Number: 4,633,024

[45] Date of Patent: Dec. 30, 1986

[54] PROCESS FOR PRODUCING AROMATIC HYDROXY COMPOUND

[75] Inventors: Ryuzo Ueno, Nishinomiya; Kazuyuki Sakota, Kobe; Yoshiyuki Naito, Shiga; Mitsuyuki Kishimoto, Yokkaichi, all of Japan

[73] Assignee: Kabushiki Kaisha Ueno Seiyaku Oyo Kenkyujo, Osaka, Japan

[21] Appl. No.: 728,453

[22] Filed: May 1, 1985

Related U.S. Application Data

[63] Continuation of Ser. No. 487,459, Apr. 22, 1983, abandoned.

[30] Foreign Application Priority Data

Apr. 23, 1982 [JP] Japan ................................. 57-67209

[51] Int. Cl.$^4$ ............................................... C07C 37/04
[52] U.S. Cl. .................................... 568/738; 568/730; 568/731; 568/737

[58] Field of Search ............... 568/759, 769, 738, 730, 568/729, 720, 719, 718, 717, 731, 737; 546/179; 564/359; 260/395

[56] References Cited

U.S. PATENT DOCUMENTS

| | | | |
|---|---|---|---|
| 2,111,973 | 3/1938 | Kokatnur | 568/769 |
| 2,334,488 | 11/1943 | Harris, Jr. et al. | 568/795 |
| 2,735,873 | 2/1956 | Goris | 568/795 |
| 2,831,895 | 4/1958 | Stevens et al. | 568/795 |

*Primary Examiner*—Nicky Chan
*Attorney, Agent, or Firm*—Sherman and Shalloway

[57] ABSTRACT

A process for producing an aromatic hydroxy compound which comprises reacting an alkali metal salt of an aromatic sulfonic acid with an alkali metal hydroxide in a reaction medium which is an aliphatic, alicyclic or aromatic hydrocarbon, or an aromatic ether or a mixture of these.

7 Claims, 1 Drawing Figure

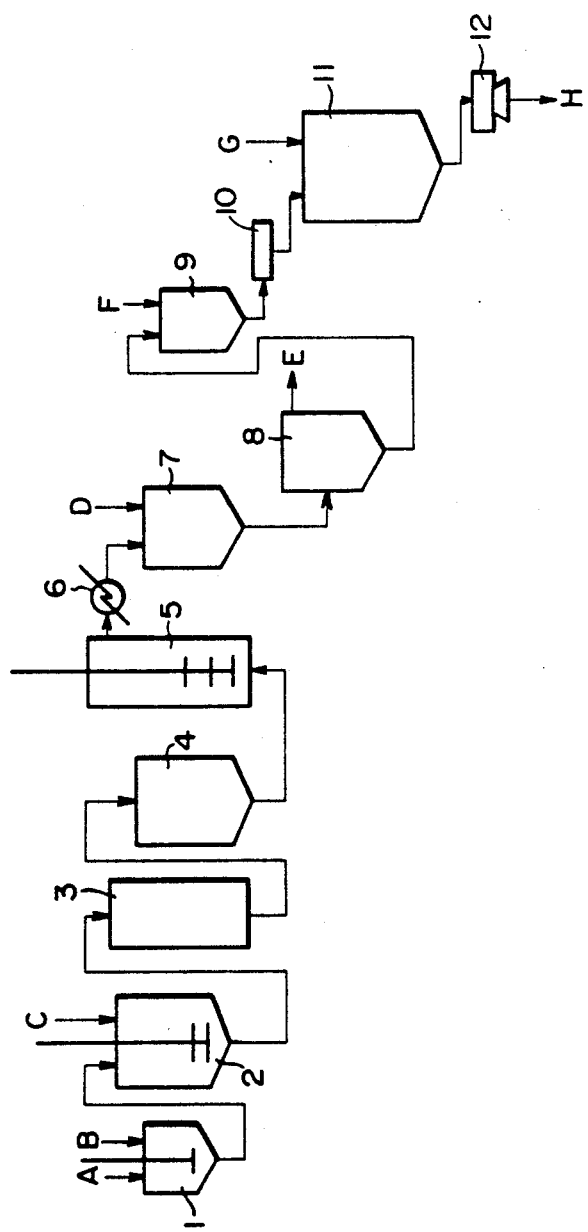

PROCESS FOR PRODUCING AROMATIC HYDROXY COMPOUND

This application is a continuation of application Ser. No. 487,459, filed Apr. 22, 1983, now abandoned.

This invention relates to an improvement in a process for producing an aromatic hydroxy compound.

There are various processes for producing aromatic hydroxy compounds. A process which first went into commercial operation comprises alkali fusion of aromatic sulfonic acid salts. Since this process is suitable for production in a small-scale apparatus, it is still utilized for the production of those aromatic hydroxy compounds whose demand is not so large. Generally, the alkali fusion is a reaction of a solid involving phase change from a liquid—a mud—a highly viscous mass—a powder, and during the reaction, stirring of the reaction mixture is extremely difficult. In order to overcome this difficulty, there have been employed a method comprising use of a powerful stirring device, a method comprising use of a multiblade kneading device, a method comprising adding an alkali during the reaction so as to maintain the reaction mixture always powdery, a method comprising performing the reaction under elevated pressures, and a method comprising carrying out the reaction in a fluidized condition by using a great excess of an alkali. The above reaction also requires high temperatures of 300° C. or more, and gives rise to many problems including the corrosion of the apparatus, the provision of a heating source, the handling of by-product alkali sulfite, and the treatment of waste liquors. It is extremely difficult therefore to utilize this reaction for mass production or continuous production in a large-sized apparatus.

The present inventors have long been engaged in a study of adapting solid-phase reactions to liquid-phase reactions, and made good achievements in the adaptation of the Kolbe-Schmitt reaction to a reaction in suspension. Further investigations into improvement of the alkali fusion of aromatic sulfonic acid salts have led to the present invention.

According to this invention, there is provided a process for producing an aromatic hydroxy compound which comprises reacting an alkali metal salt of an aromatic sulfonic acid with an alkali metal hydroxide in a reaction medium which is an aliphatic, alicyclic or aromatic hydrocarbon, or an aromatic ether, or a mixture of these.

Examples of the alkali metal salt of aromatic sulfonic acid used in this invention include alkali metal salts, such as sodium or potassium salts, of compounds having an aromatic ring, such as benzene, naphthalene, anthracene, phenanthrene, diphenyl, triphenyl, diphenylalkanes, triphenylalkanes, aromatic ring-like compounds fused with hetero rings such as a quinoline ring, and partially hydrogenated products of the foregoing compounds, having one or a plurality of sulfonic acid groups on the aromatic ring. These alkali metal salts of aromatic sulfonic acids may have one or a plurality of substituents which do not affect the reaction, such as an alkyl group, an amino group or a carboxyl group, on the ring or linking chains.

These alkali metal salts of aromatic sulfonic acids can be obtained in a customary manner by sulfonating the above-exemplified compounds having an aromatic ring with sulfuric acid or fuming sulfuric acid, and converting the sulfonated compounds to alkali metal salts.

Sodium hydroxide and potassium hydroxide are preferred as the alkali metal hydroxide. Usually, depending upon the ease or difficulty of the reaction, 2 to 10 moles, preferably 2 to 7 moles, of the alkali metal hydroxide is used per sulfonic acid group.

Suitable reaction media are aliphatic, alicyclic or aromatic hydrocarbons or aromatic ethers, include light oil, kerosene, lubricant oils, white oil (liquid paraffin), alkylbenzenes, diaryls, complete or partial hydrogenation products of diaryls, diarylalkanes, complete or partial hydrogenation products of diarylalkanes, triaryls, complete or partial hydrogenation products of triaryls, triarylalkanes, complete or partial hydrogenation products of triarylalkanes, diphenyl ether, ditolyl ether, and mixtures of two of the foregoing compounds with each other. They have a boiling point in the range of 200° to 500° C., particularly 250° to 450° C.

In performing the present invention, the alkali metal salt of aromatic sulfonic acid and the alkali metal hydroxide are dispersed in the reaction medium and reacted. For this purpose, it is preferred to dehydrate the dispersed mixture obtained by dissolving or dispersing the alkali metal salt of an aromatic sulfonic acid in an aqueous solution of the alkali metal hydroxide and adding the reaction medium or by dissolving or dispersing the alkali metal salt of an aromatic sulfonic acid in the reaction medium and adding the alkali metal hydroxide.

The amount of the reaction medium used is 0.1 to 50 parts by weight, preferably 0.5 to 20 parts by weight, per part by weight of the alkali metal salt of an aromatic sulfonic acid. The reaction temperature is 200° to 500° C., preferably 250 to 450 C. The reaction time or the residence time is about 0.1 to about 10 hours. Preferably, the reaction is carried out in an atmosphere of an inert gas such as nitrogen. It may be carried out either under atmospheric pressure or elevated pressures.

After the reaction, water is added to the reaction mixture to dissolve the resulting alkali metal salt of aromatic hydroxy compound and the excess of the alkali metal hydroxide and thus separate it into an aqueous layer and a reaction medium layer. The reaction medium layer is then separated. The aqueous solution is precipitated with an acid after, as required, the by-product sulfite, etc. are removed from it and, as required, it is subjected to a purifying operation such as decolorization. As a result, an aromatic hydroxy compound having one or a plurality of hydroxyl groups can be obtained. As desired, it can be further purified by distillation, recrystallization, etc.

According to the process of this invention, the reaction mixture can be dehydrated and reacted in a dispersed state. Hence, it can be easily dehydrated, and a uniform reaction mixture can be obtained. Consequently, the following marked improvements can be achieved by the present invention.

(1) The dehydration and reaction can be carried out continuously. Since the process can be operated while the reaction mixture is in a uniformly dispersed state, accurate temperature control and transportation become easy. Furthermore, mass production is easy because the process can be carried out completely continuously.

(2) Since the dehydration and reaction systems can be maintained uniform, the dehydration and reaction temperatures can be lowered. Furthermore, the times required for the dehydration and the reaction can be markedly shortened, and foaming of the mixture during dehydration can be inhibited. Consequently, the yield and quality of the desired product are improved.

(3) Since the amount of the alkali used can be reduced, the cost of raw materials can be curtailed. Furthermore, treatment of waste liquors can be simplified.

(4) Since the amount of the alkali used can be reduced and the contact of the alkali with the wall surface of the apparatus decreases, the corrosion of the apparatus can be inhibited, and therefore, an inexpensive material can be used to construct the apparatus.

(5) Since the reaction mixture can be easily stirred, the apparatus can be simplified, and the power required for stirring can be markedly reduced.

(6) Since the reaction mixture can be easily maintained flowable, it is not necessary to perform the reaction under high pressures in the presence of a large amount of water.

(7) Since temperature control is easy, temperature elevation and lowering can be effected easily and rapidly during the dehydration and the reaction. Hence, heat economy and operability are greatly improved.

(8) The dehydrating operation before the reaction is simplified, and can be carried out continuously.

(9) The withdrawal and the work-up of the reaction product can be simplified.

The process of this invention is industrially excellent since it can provide large quantities of the desired products of high quality at low costs.

The process of this invention can be carried out either batchwise or continuously.

The accompanying drawing is a diagram showing an embodiment of this invention by a continuous method. By using the apparatus shown in the drawing, the alkali fusion reaction and the work-up can be carried out as follows:

An aqueous solution of an alkali metal hydroxide (A) and an aromatic sulfonic acid alkali metal salt (B) are mixed with stirring in a mixing tank 1, and in a dispersing tank 2, a reaction medium C is added to disperse A and B. The dispersion is dehydrated in a dehydrating tank 3, and then a dispersed mixture composed of the alkali metal salt of aromatic sulfonic acid, the alkali metal hydroxide and the reaction medium is stored in a reservoir 4. As an alternative, it is possible to feed the reaction medium C instead of the aqueous solution of alkali metal hydroxide (A) to the mixing tank 1, and to feed the aqueous solution of alkali metal hydroxide (A) instead of the reaction medium C to the dispersing tank 2 in the above procedure. The mixture is sent to a reaction tank 5 where it is reacted with stirring at the reaction temperature and with the residence time described hereinabove. The above operation is preferably carried out in an atmosphere of nitrogen. The reaction mixture from the reaction tank 5 is preferably cooled by a heat exchanger 6, and then mixed with water D with stirring in a water-mixing tank 7. Subsequently, the mixture is separated into a reaction medium layer and an aqueous layer in a separating tank 8. The reaction medium E is recovered from the separating tank 8. The aqueous layer is transferred from the separating layer 8 to a decolorization tank 9 to decolorize it with a decolorizer F. The decolorizer is separated by a filtration device 10, and the filtrate is sent to an acid precipitation tank 11. An acid G is added to precipitate the filtrate. Finally, the desired product H is obtained by separation in a separating device such as a centrifugal separator 12.

The following non-limitative Examples illustrate the present invention specifically.

EXAMPLE 1

Biphenyl (154 g) was melted in a reaction vessel, and while it was maintained at 155° to 160° C., 392 g of concentrated sulfuric acid was added dropwise. They were reacted at this temperature for 1.5 hours. After cooling, the reaction mixture was dissolved in 2 liters of water, and an aqueous solution of potassium hydroxide was added to give 375 g of dipotassium 4,4'-biphenyldisulfonate.

Dipotassium 4,4'-biphenyldisulfonate (195 g) was added to 448 g of a 50% aqueous solution of potassium hydroxide, and the mixture was stirred. Then, 1680 g of a hydrogenated triphenyl mixture was mixed. The mixture was heated to 310° C. in an atmosphere of nitrogen, and with stirring, it was dehydrated. Thereafter, the mixture was stirred at 310° C. for 3 hours. After cooling, 1 liter of water was added to the reaction mixture to separate the triphenyl hydrogenated layer. The water layer was decolorized with activated carbon, and precipitated with dilute sulfuric acid to give 88.9 g (yield 95.6%) of 4,4'-biphenol.

EXAMPLE 2

Sodium naphthalene-2-sulfonate (230 g) was suspended in 795 g of dibenzyltoluene, and 176 g of a 50% aqueous solution of sodium hydroxide was added. The mixture was stirred under a nitrogen stream and heated to 300° C. to dehydrate it. The dehydrated mixture was stirred at 310° C. for 3 hours. After cooling, 1.2 liters of water was added to the reaction mixture to separate the reaction medium layer. The aqueous layer was decolorized with activated carbon and then precipitated with an acid to give 133.2 g (yield 92.5%) of 2-naphthol.

EXAMPLE 3

Sodium benzenesulfonate (180 g), 168 g of a 50% aqueous solution of sodium hydroxide and 480 g of a hydrogenated triphenyl mixture were mixed, and heated to 300° C. in a nitrogen stream to dehydrate the mixture. The dehydrated mixture was stirred at 320° C. for 2 hours, and then reacted at 350° to 360° C. for 1 hour. After cooling, 400 ml of water was added to separate the reaction medium layer. The aqueous layer was acidified and the precipitated bisulfite was separated by filtration. The filtrate was extracted with 100 ml of toluene and fractionally distilled to give 89.3 g (yield 95.0%) of phenol.

EXAMPLE 4

Disodium m-benzenedisulfonate (282 g), 328 g of a 50% aqueous solution of sodium hydroxide and 860 g of white oil were mixed, and heated to 300° C. in a nitrogen stream to dehydrate the mixture. The dehydrated mixture was stirred at 320° C. for 1 hour. After cooling, 400ml of water was added to the reaction mixture to separate the reaction medium layer. The aqueous layer was acidified, and the precipitated bisulfite was separated by filtration. The filtrate was extracted with 100 ml of butyl acetate, and the solvent was evaporated to give 103.8 g (yield 94.4%) of resorcinol.

EXAMPLE 5

A 50% aqueous solution of potassium hydroxide and dipotassium 4,4'-biphenyldisulfonate were sent to a mixing tank 1 at a rate of 896 kg/hr and 390 kg/hr, respectively, and mixed with stirring. A hydrogenated triphenyl mixture was added to the resulting mixture in a dispersing tank 2 at a rate of 2900 kg/hr to disperse them. The dispersed mixture was dehydrated in a dehydrating tank 3, and then sent to a reservoir. From the reservoir 4, the dehydrated mixture of dipotassium 4,4′-biphenyldisulfonate, potassium hydroxide and hydrogenated triphenyl mixture was sent to a reaction tank 5 at a rate of 4190 kg/hr, and continuously reacted at 310° C. with a residence time of 6 hours in a nitrogen stream. After the reaction, the mixture was cooled by a heat exchanger 6, and sent to a water mixing tank 7 where it was mixed with 2000 liters/hr of water. Then, in a separating tank 8, the reaction medium layer was separated, and the aqueous layer was mixed with 45 kg/hr of activated tank in a mixing tank 9. The activated carbon was removed in a filtration device 10, and the residue was precipitated with dilute sulfuric acid in an acid precipitating tank 11. By separation in a centrifugal separator 12, 178 kg (yield 95.7%) of 4,4′-biphenyl was obtained hourly.

EXAMPLE 6

Dipotassium 2,6-naphthalenedisulfonate (364 g) was added to 560 g of a 50% aqueous solution of potassium hydroxide, and the mixture was stirred. Then, 2500 g of a hydrogenated triphenyl mixture was mixed, and the resulting mixture was heated to 310° C. in a nitrogen stream and dehydrated with stirring. The mixture was then stirred at 310° C. for 3 hours. After cooling, 2 liters of water was added to the reaction mixture to separate the hydrogenated triphenyl layer. The aqueous layer was decolorized with activated carbon, and precipitated with dilute sulfuric acid to give 148.2 g (yield 92.6%) of 2,6-dihydroxynaphthalene.

EXAMPLE 7

Sodium 3,5-dimethylbenzenesulfonate (208 g) was added to 168 g of a 50% aqueous solution of sodium hydroxide, and the mixture was stirred. Then, 876 g of a hydrogenated triphenyl mixture was mixed, and the resulting mixture was heated to 310° C. in a nitrogen stream and dehydrated with stirring. The dehydrated mixture was stirred at 310° C. for 1 hour. After cooling, 800 ml of water was added to the reaction mixture to separate the reaction medium layer. The aqueous layer was acidified with dilute sulfuric acid, and extracted with 200 ml of benzene. After evaporating the benzene, the residue was distilled under reduced pressure to give 116.3g (yield 95.3%) of 3,5-dimethylphenol.

EXAMPLE 8

Trisodium 5-sulfoisophthalate (312 g) was added to 170 g of a 50% aqueous solution of sodium hydroxide, and the mixture was stirred. Then, 1980 g of 1-phenyl-1-(2,3-dimethylphenyl)-ethane was mixed, and the resulting mixture was heated to 280° C. in a nitrogen stream and dehydrated with stirring. The dehydrated mixture was stirred at 280° C. for 1.5 hours. After cooling, 1 liter of water was added to the reaction mixture to separate the reaction medium. The aqueous layer was decolorized with activated carbon, and precipitated with dilute sulfuric acid to give 172.5 g (yield 94.8%) of 5-hydroxyisophthalic acid.

EXAMPLE 9

Sodium metanilate (195 g) was added to 168 g of a 50% aqueous solution of sodium hydroxide, and the mixture was stirred. Then, 1156 g of light oil was mixed, and the resulting mixture was heated to 260° C. in a nitrogen stream and dehydrated with stirring. The dehydrated mixture was stirred at 260° C. for 1 hour. After cooling, 500 ml of water was added to the reaction mixture to separate the reaction medium layer. The aqueous layer was decolorized with activated carbon, and precipitated with an acid. The crystals were collected by filtration. The mother liquor was extracted with 200 ml of ether. The ether was recovered, and the residue was combined with the crystals obtained above to give 102.7 g (yield 94.2%) of m-aminophenol.

EXAMPLE 10

Sodium quinoline-8-sulfonate (231 g) was added to 170 g of a 50% aqueous solution of sodium hydroxide, and the mixture was stirred. Then, 900 g of a hydrogenated triphenyl mixture was mixed, and the mixture was dehydrated. The dehydrated mixture was reacted at 260° C. for 15 minutes in a nitrogen stream. After cooling, 600 ml of water was added to the reaction mixture to separate the reaction medium layer. The aqueous layer was decolorized with activated carbon, acidified and then extracted with 200 ml of chloroform. The chloroform was recovered to give 140.9 g (yield 97.2%) of 8-hydroxyquinoline.

EXAMPLE 11

Disodium 2-hydroxynaphthalene-3,6-disulfonate (348 g) was added to 176 g of a 50% aqueous solution of sodium hydroxide, and the mixture was stirred. Then, 900 g of a hydrogenated triphenyl mixture was mixed, and the resulting mixture was dehydrated. The dehydrated mixture was reacted at 270° C. for 1.5 hours in a nitrogen stream. After cooling, 2 liters of water was added to the reaction mixture to separate the reaction medium layer. The aqueous layer was decolorized with activated carbon, and then precipitated with an acid to give 231 g (yield 96.3%) of 2,3-dihydroxynaphthalene-6-sulfonic acid.

EXAMPLE 12

Sodium naphthalene-2-sulfonate and a hydrogenated triphenyl mixture were sent to a mixing tank 1 at a rate of 230 kg/hr and 825 kg/hr, respectively, and mixed with stirring. In a dispersing tank 2, 200 kg/hr of a 50% aqueous solution of sodium hydroxide was added to form a dispersed mixture. The dispersed mixture was dehydrated in a dehydrating tank 3, and sent to a reservoir 4. From the reservoir 4, a mixture consisting of sodium naphthalene-2-sulfonate, sodium hydroxide and the hydrogenated triphenyl mixture was sent to a reaction tank 5 at a rate of 1155 kg/hr, and continuously reacted at 310° C. in a nitrogen stream with a residence time of 6 hours. After the reaction, the reaction mixture was cooled in a heat exchanger 6, and sent to a water mixing tank 7 where it was mixed with 1200 liters/hr of water. Then, the reaction medium layer was separated in a separating tank 8, and the aqueous layer was mixed with 3.1 kg/hr of activated carbon in a mixing tank 9. Then, the activated carbon was removed in a filtration device 10. The residue was precipitated with dilute sulfuric acid in an acid precipitation tank 11, and separated by a centrifugal separator 12 to give 137.2 g (yield 95.3%) of 2-naphthol hourly.

What is claimed is:

1. In a process for producing an aromatic hydroxy compound which comprises reacting an alkali metal salt of a corresponding aromatic sulfonic acid with an alkali metal hydroxide in a reaction medium, the improvement which comprises using as the reaction medium at least one member selected from the group consisting of diarylalkanes, complete and partial hydrogenation products of diarylalkanes, triaryls, complete and partial hydrogenation products of triaryls, triarylalkanes, and complete and partial hydrogenation products of triarylalkanes, wherein the aromatic ring structure of said aromatic sulfonic acid is a naphthalene or diphenyl ring.

2. The process of claim 1 wherein 0.1 to 50 parts by weight of the reaction medium is used per part by weight of the alkali metal salt of the aromatic sulfonic acid.

3. The process of claim 1 or 2 wherein 2 to 10 moles of the alkali metal hydroxide is used per sulfonic acid group of the alkali metal salt of the aromatic sulfonic acid.

4. The process of claim 3 wherein the reaction is carried out at a temperature of 200° to 500° C.

5. The process of claim 1 or 2 wherein the reaction is carried out at a temperature of 200° to 500° C.

6. The process of claim 1 wherein the alkali metal salt of the aromatic sulfonic acid is selected from the group consisting of dipotassium 4,4'-biphenyldisulfonate, sodium naphthalene-2-sulfonate and dipotassium 2,6-naphthalenedisulfonate.

7. The process of claim 1 or 6 wherein the reaction medium is selected from the group consisting of hydrogenated triphenyl, and 1-phenyl-1-(2,3-dimethylphenyl)-ethane.

* * * * *